United States Patent
Laurell et al.

(10) Patent No.: US 9,656,263 B2
(45) Date of Patent: May 23, 2017

(54) SYSTEM AND METHOD TO SEPARATE CELLS AND/OR PARTICLES

(71) Applicant: ACOUSORT AB, Lund (SE)

(72) Inventors: Thomas Laurell, Lund (SE); Carl Grenvall, Lund (SE); Cecilia Magnusson, Malmö (SE); Per Augustsson, Lund (SE)

(73) Assignee: ACOUSORT AB, Lund (SE)

( * ) Notice: Subject to any disclaimer, the term of this patent is extended or adjusted under 35 U.S.C. 154(b) by 0 days.

(21) Appl. No.: 14/347,793

(22) PCT Filed: Sep. 27, 2012

(86) PCT No.: PCT/SE2012/051028
§ 371 (c)(1),
(2) Date: Mar. 27, 2014

(87) PCT Pub. No.: WO2013/048323
PCT Pub. Date: Apr. 4, 2013

(65) Prior Publication Data
US 2014/0231315 A1    Aug. 21, 2014

Related U.S. Application Data

(60) Provisional application No. 61/540,217, filed on Sep. 28, 2011.

(30) Foreign Application Priority Data

Sep. 28, 2011 (SE) ........................... 1150889

(51) Int. Cl.
*G01N 1/28* (2006.01)
*B01L 3/00* (2006.01)
(Continued)

(52) U.S. Cl.
CPC .......... *B01L 3/502761* (2013.01); *B03B 7/00* (2013.01); *G01N 1/4077* (2013.01);
(Continued)

(58) Field of Classification Search
CPC .................. B07C 5/34; G01N 1/4094; G01N 2015/1081; G01N 2015/1087;
(Continued)

(56) References Cited

U.S. PATENT DOCUMENTS

| 4,523,682 A | * | 6/1985 | Barmatz | B01D 21/283 |
| | | | | 181/0.5 |
| 5,711,888 A | * | 1/1998 | Trampler | B01D 21/283 |
| | | | | 210/748.05 |

(Continued)

FOREIGN PATENT DOCUMENTS

| JP | 07047259 | 2/1995 |
| WO | 85/01892 A1 | 5/1985 |

(Continued)

OTHER PUBLICATIONS

Extended European Search Report dated Jun. 19, 2015, corresponding to EP 12837014.5-1404 / 2761291, PCT/SE1012051028.
(Continued)

*Primary Examiner* — Joseph C Rodriguez
(74) *Attorney, Agent, or Firm* — Harness, Dickey & Pierce, P.L.C.

(57) ABSTRACT

The invention provides a micro scaled method and system for separating a subgroup of cells and/or particles from a mixture of different types of cells and/or particles in a suspension. The suspension is forced under pressure into an inlet and further into a pre-alignment channel wherein the suspension is subjected to a two dimensional acoustic force directed perpendicular to the length direction of the pre-alignment channel. The suspension is then forced into a (Continued)

second inlet and further into at least one separation channel wherein the mixture of cells and/or particles are forced towards the walls of the channel and subjected to a one dimensional acoustic force directed perpendicular to the length direction of the separation channel. Cells and/or particles having the same size and/or mass density and/or compressibility are collected through at least two outlets.

15 Claims, 10 Drawing Sheets

(51) Int. Cl.
G01N 33/50 (2006.01)
G01N 33/543 (2006.01)
G01N 33/574 (2006.01)
B03B 7/00 (2006.01)
G01N 1/40 (2006.01)
G01N 15/00 (2006.01)

(52) U.S. Cl.
CPC ... *G01N 33/5005* (2013.01); *G01N 33/54313* (2013.01); *G01N 33/574* (2013.01); B01L 2200/0652 (2013.01); B01L 2300/0816 (2013.01); B01L 2300/0864 (2013.01); B01L 2400/0436 (2013.01); G01N 2001/4094 (2013.01); G01N 2015/0053 (2013.01)

(58) Field of Classification Search
CPC ....... G01N 2015/149; G01N 200/4094; G01N 2015/1491; B01L 3/502761; B01L 2400/0436; B01L 2400/0439
See application file for complete search history.

(56) References Cited

U.S. PATENT DOCUMENTS

| | | | |
|---|---|---|---|
| 8,266,951 B2* | 9/2012 | Kaduchak | G01N 15/1404 73/570.5 |
| 8,387,803 B2* | 3/2013 | Thorslund | B01L 3/502761 209/552 |
| 2009/0042310 A1* | 2/2009 | Ward | G01N 15/1404 436/154 |
| 2009/0178716 A1 | 7/2009 | Kaduchak et al. | |
| 2009/0226994 A1* | 9/2009 | Lemor | B01L 3/502715 435/173.1 |
| 2010/0126922 A1* | 5/2010 | Takahashi | B01D 21/283 210/201 |
| 2010/0138377 A1 | 6/2010 | Wright et al. | |
| 2010/0139377 A1* | 6/2010 | Huang | B01L 3/502761 73/61.75 |
| 2011/0154890 A1* | 6/2011 | Holm | B01D 21/283 73/61.75 |
| 2013/0000420 A1* | 1/2013 | Manneberg | B01J 19/0046 73/863 |
| 2013/0029407 A1 | 1/2013 | Terazono et al. | |
| 2014/0008307 A1* | 1/2014 | Guldiken | B01L 3/502761 210/748.05 |

FOREIGN PATENT DOCUMENTS

| | | |
|---|---|---|
| WO | 2006/031299 A2 | 3/2006 |
| WO | 2007/006322 A1 | 1/2007 |
| WO | 2007/128795 A2 | 11/2007 |
| WO | WO-2010123453 A1 | 10/2010 |
| WO | 2011/068764 A2 | 6/2011 |

OTHER PUBLICATIONS

Jonathan D. Adams et al, "Tunable Acoustophoretic Band-Pass Particle Sorter", Applied Physics Letters, Aug. 13, 2010, pp. 64103-1-64103-3, vol. 97, No. 6, American Institute of Physics, US.
Zhuochen Wang et al, "Recent Advances in Particle and Droplet Manipulation for Lab-On-A-Chip Devices Based on Surface Acoustic Waves", Lab on a Chip, Feb. 8, 2011, pp. 1280-1285, vol. 11, The Royal Society of Chemistry, http://pubs.rsc.org/doi:10.1039/C0LC00527D, GB.
Per Augustsson et al, "Decomplexing Biofluids Using Mirochip Based Acoustophoresis", Lab on a Chip, Jan. 1, 2009, pp. 810-818, vol. 9, No. 6, The Royal Society of Chemistry, GB.
Per Augustsson et al, "Microfluidic, Label-Free Enrichment of Prostate Cancer Cells in Blood Based on Acoustophoresis", Analytical Chemistry, Sep. 18, 2012, pp. 7954-7962, vol. 84, No. 18, ACS Publications, US.
International Search Report for PCT/SE2012/051028, ISA/SE, Stockholm, mailed Jan. 2, 2013.
Manneberg O. et al., Wedge transducer design for two-dimensional ultrasonic manipulation in a microfluidic chip, Journal of micromechanics and microengineering 2008, 18 (095025), 1-9; abstract; See Introduction part, as well as paragraph 4.2.2 and figure 7.
Manneberg O. et al., Spatial confinement of ultrasonic force filds in microfluidic chanels, Ultrasonics, 2009 49, 112-119; abstract; See paragraph 4.2 and figure 2.
Laurell T. et al., Chip integrated strategies for acoustic separation and manipulation of cells and particles, Chemical Society Reviews 2007, 36, 492-506; abstract; See "Conclusion and outlook" and figures: 7, 22 and 25.
Peterson F. et al., Free flow acoustophoresis: Microfluidic- based mode of particle and cell separation, Analytical chemistry, 2007, 79 (14), 5117-5123; abstract; p. 5118, col. 1.
Jung B. et al., Acoustic particle filter with adjustable effective pore size for automated sample preparation, Analytical Chemistry, 2008, vol. 80, No. 22, pp. 8447-8452; abstract; See last paragraph p. 8447-first paragraph p. 8449; p. 8450: "results and discussion"; p. 8451-8452: "Summary".
T. Laurell et al.; Chip Integrated Strategies for Acoustic Separation and Manipulation of Cells and Particles; Chem. Soc. Rev. 2007, V36; 492-506.

* cited by examiner

SYSTEM AND METHOD TO SEPARATE CELLS AND/OR PARTICLES

CROSS REFERENCE TO RELATED APPLICATIONS

This application is a 371 U.S. National Stage of International Application No. PCT/SE2012/051028, filed Sep. 27, 2012, which claims priority to Swedish Patent Application No. SE 1150889-2, filed Sep. 28, 2011 and which claims the benefit of U.S. Provisional Application No. 61/540,217, filed Sep. 28, 2011. The entire disclosures of the above applications are incorporated herein by reference.

FIELD OF THE INVENTION

The invention relates to a method and system to separate a subgroup of cells and/or particles from a mixture of cells and/or particles present in a suspension wherein said suspension if exposed to acoustic forces acting in one or two dimensions, which forces said cells and/or particles to separate from each other into groups which have similar properties in connection with size and/or mass density and/or compressibility.

BACKGROUND OF THE INVENTION

Microfluidics is inherently a domain where high performance cell and particle handling has proven to be very successful. Some of the ruling technology platforms, which are industrial and clinical standards for high quality cell processing, are found in the fluorescence activated cell sorter (FACS) (Fluorescent detection and sorting) and in the Coulter Counter (size distribution measurements). The combination of fluorescently labeled cell specific antibodies and the FACS technique opened the route to a revolution in modern cell biology. However, all problems could still not be solved by that technique, such as sorting specific cells from a population of cells wherein no marker is used and thereby there are no biomolecular modifications or other perturbation of the cells.

Extensive studies have explored passive hydrodynamic techniques to separate cells and particles such as deterministic lateral displacement, hydrodynamic filtration, hydrophoretic separation and pinched flow fractionation. These techniques are solely dependent on the fluid dynamic properties of the separation channel in relation to the particle size. These techniques commonly display good separation properties but suffer from low throughput as particle concentration has to be low in order to achieve good separation. To overcome these problems a number of alternative approaches including split thin flow fractionation, magnetophoresis, optical methods as well as dielectrophoresis have been investigated. A common feature of these approaches is that particles/cells are separated by means of an applied force field directed transversely to the direction of the general flow direction in order to cause selective deflection of particle/cell trajectories. However, all these techniques have so far not managed to separate cells with a high degree of particle/cell discrimination and/or at particle throughputs that are sufficient for a broad applicability in life science applications. Acoustophoresis has also been shown to perform particle/cell separation by the use of acoustic force fields acting on particles in suspension. Acoustophoresis suffers to a less extent of throughput limitations, nor is it highly dependent of ionic strength or pH as compared to e.g. dielectrophoretic techniques.

A common problem when using microchannels for separation of species in aqueous suspensions is that of dispersion, due to the laminar flow conditions, associated with small length scales. The laminar flow implies that the fluid velocity (u) in the length direction (x) of such a channel depend on the spatial position relative to the channel width (y-direction) and height (z-direction). Near the walls the velocity approaches zero while in the bulk, the flow velocity is higher. Hence, the retention time in the channel for a particle/cell will, in effect, be dictated by its initial lateral position (y and z). I.e. cells/particles entering at different positions in the transverse cross section of the channel will pass through the channel at different speed. Separation can only be truly deterministic if particles/cells enter the separation channel in the exact same lateral position, and thereby flow through the separation channel at equal speed. Thus the particle/cell position at the end of such separation channel is a function of the initial position of the particle/cell and the employed external force field.

A prerequisite to fulfill the requirement for a deterministic separation outcome is that cells/particles are pre-aligned in the yz-plane of the fluid flow prior to entering into the channel region which encompasses the actual separation step. Pre-alignment can be accomplished by employing external forces in two dimensions along the y- and z-axis.

US2009/0042310 discloses the separation of particles by the use of an acoustic force, wherein said acoustic force is a one dimensional force applied two times to separate cells, wherein they are moving particles in a flow rate.

Mannebeg O et al., J of micromechanics and microengineering, 2008, 18, page 1-9 discloses how one dimensional forces in both the x and the y axis.

Several strategies have been proposed to isolate circulating tumor cells (CTCs) such as physical e.g. physical structures in the channel that captures the tumor cells, and biochemical affinity based approaches involving microbeads or micro-posts. To date, most successful techniques to enrich CTCs from metastatic cancer patients depend on immuno-labeling. Epithelial cells in general, and the majority of epithelial derived tumor cells express the epithelial cell adhesion protein (EpCAM) and different cytokeratines (CK), which are absent in normal blood cells. These markers are vastly used in the available CTC isolation methods. However, a drawback is the exclusion of EpCAM or CK negative CTCs. The substantial variations in both morphology and antigen expression among CTCs consequently call for innovative approaches to enhance CTC enrichment. The invention is focused on the above defined drawbacks with the systems.

SUMMARY OF THE INVENTION

Acoustic standing wave force fields have been used extensively to focus/concentrate cells in microfluidic system, utilizing the fact that the flow channel serves as the fluid conduit at the same time as it acts as an acoustic resonator defined by the channel dimension. Efforts to separate different particles in acoustic force-fields based on their intrinsic acoustophysical parameters have been reported but have still suffered from the parabolic flow profile causing a variation in retention time in the force field performing the separation step. At the time point when the invention was made it was common knowledge that it was not possible to create two acoustic waves using one and the same frequency and solely by coincidence the inventors tried that and found that it worked at the frequencies they are using. A person skilled in the art would not even have tried since if you start calculating it should in theory not be possible.

The current invention discloses how pre-alignment of cells and particles may be performed by designing a channel such that an acoustic standing wave force field act on cells/particles in both two dimensions and one dimensions, i.e., three dimensions. By the use of first a two dimensional force in combination with the introduction of a cell free buffer solution followed by a one dimensional force it is possible to separate and focus cells into specific separation paths with higher resolution compared to before.

Pre-aligned particles/cells subsequently enter into a microchannel segment designed for an acoustic standing wave resonance mode, which yields a force field that performs the cell/particle separation along a single dimension. The pre-alignment of cells/particles ensures equal retention time in the separation zone, and hence problems commonly experienced in poor separation resolution due to the parabolic flow profile of laminar flow conditions are alleviated.

In one aspect the invention relates to a micro scaled method for separating a subgroup of cells and/or particles from a mixture of different types of cells and/or particles in a suspension, comprising the steps of i) subjecting a suspension to pressure, wherein said pressure forces said suspension into at least one inlet (11) and into at least one pre-alignment channel present on a microfluidic chip, ii) subjecting said suspension to a two dimensional acoustic force directed perpendicular to the length direction of the pre-alignment channel (15), iii) forcing said mixture of cells and/or particles and infusing cell free buffer solution through a second inlet (12) simultaneously into at least one separation channel, wherein said mixture of cells and/or particles are forced towards the walls of the channel, iv) subjecting said cells and/or particles to a one dimensional acoustic force directed perpendicular to the length direction of the separation channel (16) and v) collecting cells and/or particles having the same size and/or mass density and/or compressibility, at the end of the separation channel present on the microfluidic chip through at least two outlets (13, 14).

In another aspect the invention relates to a micro system for separating a subgroup of cells and/or particles from a mixture of different types of cells and/or particles in a suspension, comprising;

i) a microchip having at least one pre-alignment channel (15) and at least one separation channel (16), with at least two inlets (11, 12) and at least two outlets (13, 14), ii) means for providing pressure, wherein said pressure forces said suspension into the first inlet (11), iii) means for providing a two dimensional acoustic force, wherein said two dimensional acoustic force is directed perpendicular to a pre-alignment channel (15), iv) means for infusing cell-free buffer in said second inlet (12), v) means for providing one dimensional acoustic force, wherein said one dimensional acoustic force is directed perpendicular to the separation channel (16) and vi) means for collecting objects having the same size and/or mass density and/or compressibility from at least two outlets (13, 14).

For the first time it is possible to increase the resolution in a micro system to such levels that even small differences between cells and/or particles makes them separable. This is achieved by introducing a two-dimensional acoustic force field in at least one pre-alignment microchannel where cells/particles can be directed into a defined position in the y-z-plane. This confines particles/cells to one or more discrete positions in the plane transverse to the flow, prior to entering the separation channel, hence making the separation deterministic such that the intrinsic properties of the particles/cells and the fluid dynamic interaction between particle/cell and the aqueous medium governs the separation outcome. The combined effect of pre-alignment and separation will thus increase the resolving power of such systems and enables for the first time the possibility to separate closely related cells from each other as shown in the examples.

DETAILED DESCRIPTION OF THE INVENTION

Definitions

Letters (x), (y) and (z) refers to the spatial position along the length (l), width (w), and the height (h) of the microchannel, respectively. Letters $(Q_i)$, (v), and $(p_i)$ refers to volume flow rate, flow velocity and pressure, respectively where subscript (i) indicate multiple instances of a property. The word suspension refers to a fluid containing solid particles or cells that are sufficiently large for sedimentation.

Methods and System

The invention relates to methods and systems for separating a subgroup of objects such as cells and/or particles from a suspension.

Method I

Figure 1:
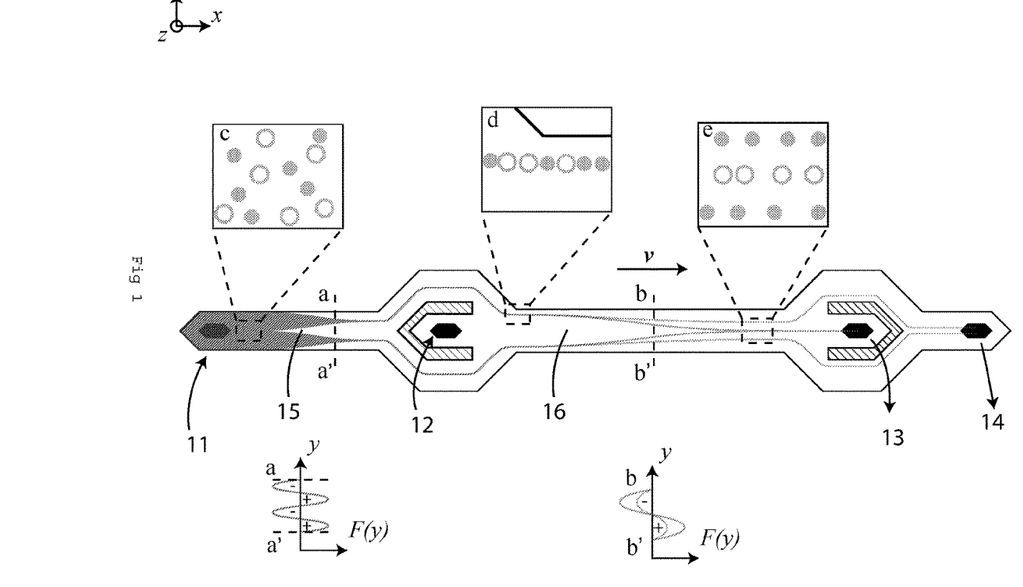
FIG. 1. Schematic of on-chip transport of two suspended species. Top view. Not to scale.
Figure 2:
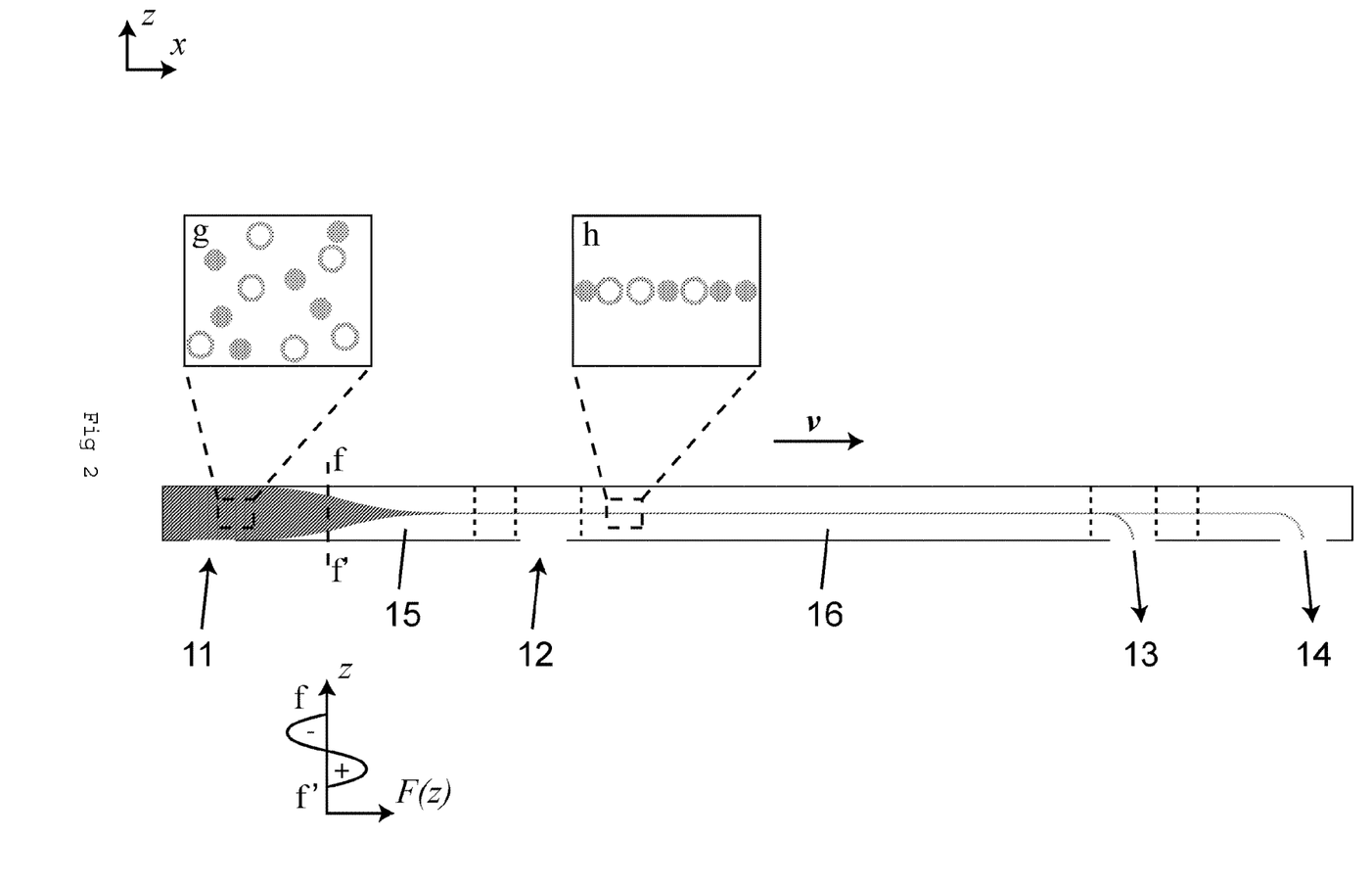
FIG. 2. Schematic of on-chip transport of two suspended species. Side cross-sectional view. Not to scale.

In one aspect the invention relates to a method, which comprises the steps of;

a) Forcing a suspension (51) via tubing (55) into at least one pre-alignment channel (15) by elevating the hydrostatic pressure $p_1$ in the container of the suspension (51) such that the pressure at the channel inlet (11) is higher than the pressure at any of the other fluidic connections (12, 13, and 14). Said pressure difference cause a laminar flow in the channel that may be varied from 1 μL/min to 2 mL/min. The elevated pressure may be established using a syringe pump, a peristaltic pump, or by regulating the gas pressure in a sealed chamber wherein the container of the fluid is placed.

b) Subjecting the suspended objects (FIG. 1, inset c) in said suspension to a two-dimensional acoustic force potential (FIG. 1, a-a' and FIG. 2, f-f') directed perpendicular to the pre-alignment channel (15), so that all of the cells and/or particles are localized into one or more points in the transverse cross-section of the flow. The two-dimensional acoustic force potential stems from resonant modes of ultrasound inside the water filled channel caused by reflections in the interface between the acoustically soft water and the acoustically hard walls of the channel. By tuning the frequency of the ultrasound vibrations, modes can be excited that forces suspended cells and/or particles away from the walls, floor and ceiling of the channel towards the nearest vibrational pressure node. The constant influx of suspension at (11) in combination with the two-dimensional acoustic force potential causes the cells and/or particles of the suspension to align in narrow bands just before exiting the pre-alignment channel (FIG. 1, inset d and FIG. 2, inset h).

The pre-alignment channel may have a width and/or height ranging from 75 μm to 800 μm, such as from 75 μm to 200 μm, or ranging from 200 μm to 375 μm, or ranging from 300 μm to 400 μm, or ranging from 400 μm to 700 μm, or ranging from 700 μm to 800 μm, or being 150 μm, 300 μm, 188 μm, 375 μm or 750 μm.

The width and height of the pre-alignment channel may be related such that the width w divided by an integer number n equals the height h divided by an integer number m. In this case a single frequency of vibration may be chosen to fulfill a resonance condition simultaneously for the height and width dimension, such that $$f = \frac{cn}{2w} = \frac{cm}{2h}$$

there c is the speed of sound in the suspending fluid.

If the width and height of the channel are not related, the resonance condition may be controlled individually/selectively using separate frequencies of vibration for height and width, respectively. The frequency of vibration may vary in a range from 1 MHz to 10 MHz and is implicitly dictated by the dimensions of the channel as mentioned above and by choosing, either n=1, m=2, c=1500 m/s. Other examples are from 1-5 MHz, such as from 2-5 MHz or being 2 MHz or 5 MHz.

One example of this two-dimensional acoustic force potential is when a water filled pre-alignment channel (15) of width $w_{15}$=300 μm and height h=150 μm for a vibrational frequency $f_{15}$=5 MHz. For a stipulated speed of sound c in the suspension of 1500 m/s, the acoustic wavelength $\lambda_{15}$=c/$f_{15}$=300 μm. Given that the channel only can support multiples of half wavelengths it is clear that the vibration can induce resonance in the channel both along the y-axis (FIG. 1, a-a') and along the z-axis (FIG. 2, f-f'). The combined yz-mode will have two vibrational pressure minima at ($y_1$, $z_1$)=($w_{15}$/4, h/2) and ($y_2$, $z_2$)=(3 $w_{15}$/4, h/2).

c) Forcing said acoustically pre-focused suspension and infusing particle free liquid via a central inlet (12) simultaneously into a second separation channel (16), wherein said mixture of cells and/or particles are forced to proximity of one or more walls of said second channel. The suspension is thus laminated along one or both sides of an acoustophoresis microchannel while particle free liquid occupies the remaining part of the channel. The relative volume flow rates $Q_2$ and $Q_1$, of the particle free liquid and the suspension, respectively, determine the lateral position (y=$w_1$) of the cells and/or particles, when entering the second channel (16). Increase of $Q_2$ leads to a decrease of $w_1$. The motive for doing so will be clear in paragraph (d and e).

d) Subjecting said mixture of cells and/or particles to a one dimensional acoustic force potential directed primarily along the y-axis of said separation channel, so that all of the objects move towards the vertical center plane of that channel. The one dimensional acoustic force potential stems from a resonant mode of ultrasound inside the water filled channel caused by reflections in the interface between the acoustically soft water and the acoustically hard walls of the channel. By tuning the frequency of the ultrasound vibrations, a half wavelength resonance mode can be excited that forces suspended objects away from the walls of the channel towards the vibrational pressure node in the channel center. The objects, that have previously been aligned by the 2-dimensional pre-alignment channel and are in proximity of the walls, move towards the central vibrational pressure minima in the center of the channel.

The separation channel may have a width ranging from 75 μm to 800 μm, such as from 75 μm to 200 μm, or ranging from 200 μm to 375 μm, or ranging from 300 μm to 400 μm, or ranging from 400 μm to 700 μm, or ranging from 700 μm to 800 μm, or being 150 μm, 300 μm, 188 μm, 375 μm or 750 μm.

The width may be chosen such that the frequency of vibration f is $$f = \frac{cn}{2w}$$

there c is the speed of sound in the suspending fluid.

The frequency of vibration may vary in a range from 1 MHz to 10 MHz and is implicitly dictated by the specified dimensions of the channel as mentioned above and by choosing n=1 and c=1500 m/s.

One example of this one-dimensional acoustic force potential can be a water filled separation channel (16) of width $w_{16}$=375 μm and height h=150 μm for a frequency of vibration $f_{16}$=2 MHz. For a stipulated speed of sound c in the suspension of 1500 m/s, the acoustic wavelength $\lambda_{16}$=c/$f_{16}$=750 μm. Given that the channel only can support multiples of half wavelengths it is clear that the vibration only can induce resonance in the channel along the y-axis (FIG. 1, b-b'). This mode will have one vibrational pressure minima at y=$w_{16}$/2.

Each cell and/or particle move in the x-direction along the channel driven by the flow, while being forced towards the central vibrational node, in the y-direction, at a rate that is determined by the acoustomechanical properties, mass density and compressibility of the suspending medium and the cell and/or particle, respectively. The rate is also determined by the size of the cell and/or particle and the strength of the acoustic resonance. By tuning the amplitude of the acoustic resonance in the second channel, the paths of the cells and/or particles may be deflected so that cells and/or particles of dissimilar acoustic mobility exit the channel at different locations along the y-axis.

Figure 6:
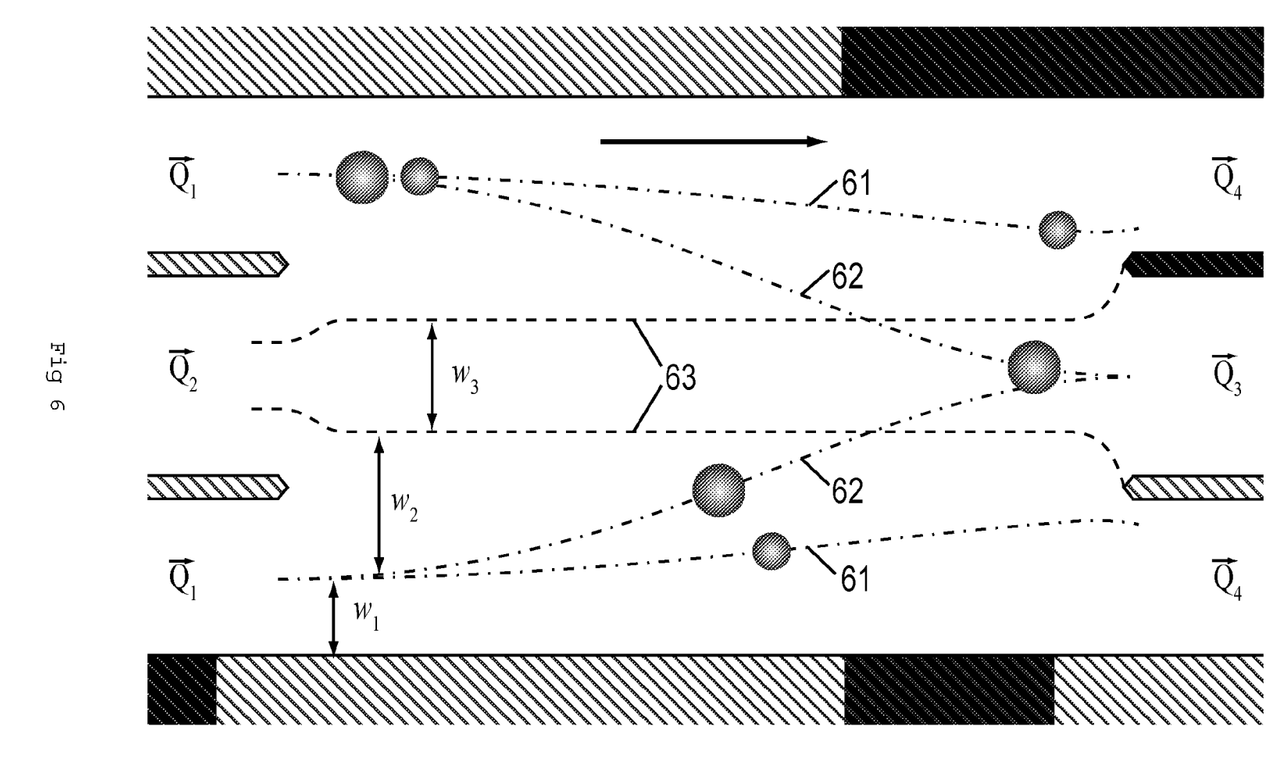
FIG. 6. Outlet flow split ratio

Since all cells and/or particles are pre-aligned in the yz-plane when entering the separation channel, their individual trajectories, reflect their acoustophysical properties and size, to a high degree. In absence of the pre-alignment the trajectories of individual cells and/or particles would be strongly influenced by their initial position when entering the separation channel, which is indeed not an intrinsic property of the cell and/or particle.

e) Adjusting the volume flow rates in the inlets (FIG. 6, $Q_1$ and $Q_2$) and outlets $Q_3$ and $Q_4$ to maximize the travel distance ($w_2$) at the cost of processing time. By imposing a longer travel distance for a cells and/or particles to reach the central outlet (13), the number of faulty cells and/or particles in that outlet will be reduced. Decreasing $Q_3$ relative to $Q_4$ will narrow down the hydrodynamic aperture ($w_3$) of the central outlet and cause an increased ($w_2$). Similarly, decreasing $Q_1$ relative to $Q_2$ will diminish ($w_1$). The increased selectivity must be balanced against the demands regarding processing time of a sample of some finite volume, which is related to $Q_1$, and the ability of the external fluidics to produce a stable enough flow, which is related to $Q_3$ relative any disturbance in $Q_4$.

Method II

Figure 7:
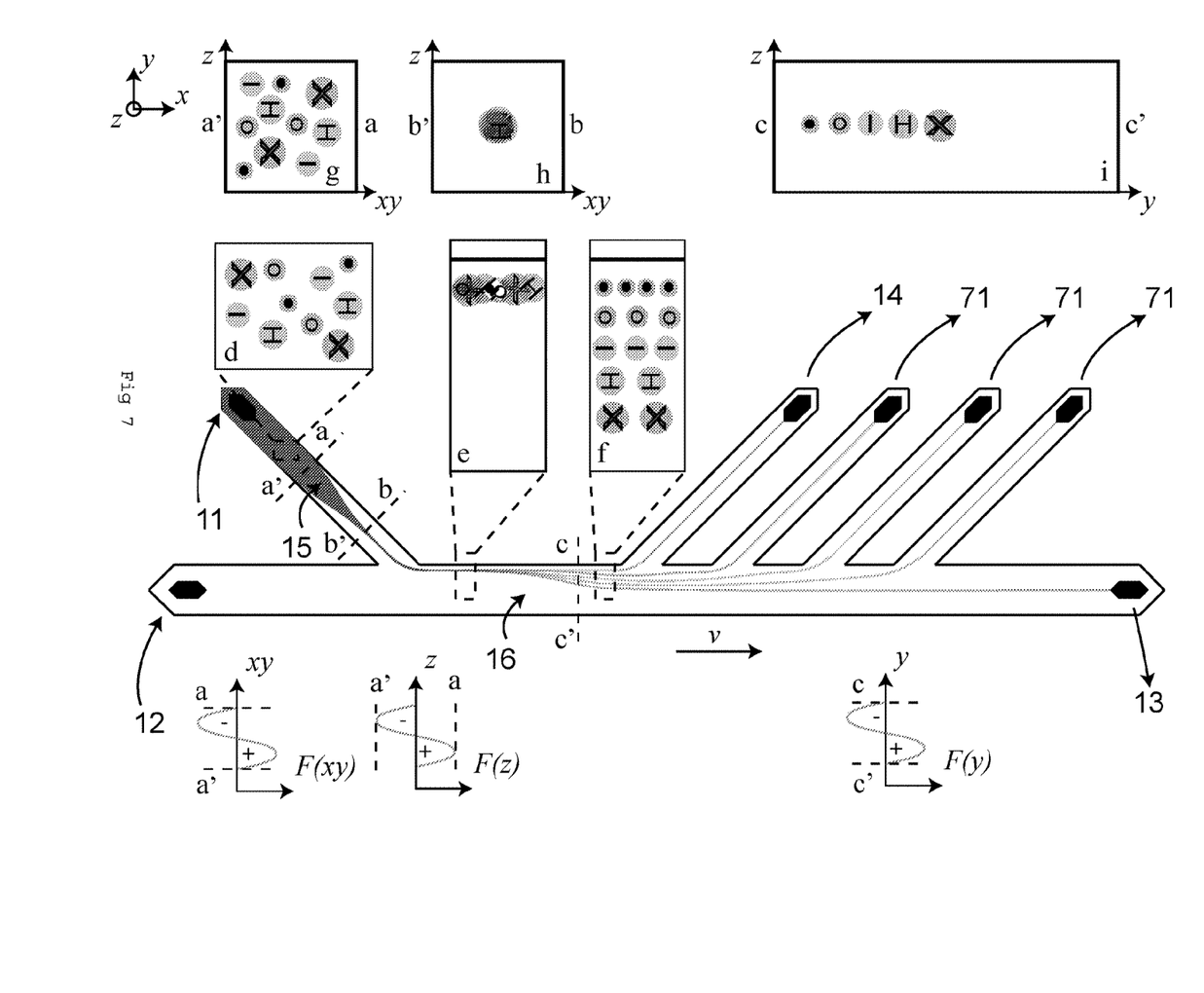
FIG. 7. Single sided FFA

In a second aspect the invention relates to a method, which comprises the steps of;

a) Forcing a suspension (51) via tubing (55) into at least one pre-alignment channel (15) by elevating the hydrostatic pressure $p_1$ in the container of the suspension (51) such that the pressure at the channel inlet (11) is higher than the pressure at any of the other fluidic connections (12, 13, 14, and 71). Said pressure difference cause a laminar flow in the channel that may be varied from 1 μL/min to 2 mL/min. The elevated pressure may be established using a syringe pump, a peristaltic pump, or by regulating the gas pressure in a sealed chamber wherein the container of the fluid is placed.

b) Forcing a suspension of cells and/or particles into a pre-alignment channel, (11), subjecting the suspended cells and/or particles in said suspension to a two dimensional acoustic force potential directed perpendicular to said pre-alignment channel (FIG. 7, insert d). Thereby all of the particles are being pre-aligned into one point, simultaneously centered in the xy-plane as well as the z-plane in the transverse cross section of the flow (FIG. 7, insert e). The laminar flow profile, dominating at previously mentioned flow speeds and channel dimensions, contains the focused cells and/or particles in said point after pre-alignment.

One example of the implementation of a two dimensional force potential to improve acoustic force driven separation of cells and/or particles in a suspension may be a water filled channel segment, (15), of width $w_2$=150 μm and height h=150 μm, designed for a resonance frequency f=5 MHz. For a stipulated speed of sound c in the suspension of 1500 m/s, the acoustic wavelength λ=c/f=300 μm and hence the square channel cross section can then support a half wavelength standing wave both in the height (z) and in the width (xy) direction.

c) Forcing said pre-aligned cells and/or particles in the suspension into the channel, which may have a width $w_3$=375 μm and height $h_2$=150 μm, having a laminar main buffer flow entering from (12), while still maintaining low enough total flow (pre-aligned flow+main buffer flow) to maintain a laminar flow regime in the channel, thus laminating the pre-aligned cells and/or particles stream along the side wall of said second channel (FIG. 7, insert e). Said channel may be designed for a resonance frequency f=2 MHz. For a stipulated speed of sound c in the suspension of 1500 m/s, the acoustic wavelength λ=c/f=750 μm and hence the rectangle channel cross section (c-c') can then only support a half wavelength standing wave in the width (y) direction.

d) Subjecting said pre-aligned stream of cells and/or particles to a one dimensional acoustic force potential directed perpendicular to said second channel (c-c'), so that all of the objects move towards one point, along the y-plane, in the transverse cross section of the flow (FIG. 7, insert f). The point toward which the cells and/or particles, previously aligned by the 2-dimensional pre-alignment and now in proximity of the sidewall, move towards, is the central vibrational pressure minima in the center of the channel as determined by the previously mentioned channel width $w_3$ and acoustic resonance frequency at the stipulated speed of sound. The difference in transport velocity, between particles, to the center of the second channel is determined by the difference in material properties of the particle i.e. size, density and speed of sound. Hence under constant acoustic amplitude and buffer conditions, the lateral position (FIG. 7, insert f and i) of the cells and/or particles in the channel will determine which outlets (13), (14), (71) that the cells and/or particles exit the system. By adjusting the number of outlets, flow speeds and acoustic effect, it is then possible to direct a fraction of the laminar flow towards a specific outlet. This allows to discriminate extraction of certain cells and/or particles according to any of the previously mentioned acoustic properties as well as size.

e) Collecting cells and/or particles having the same size and/or mass density and/or compressibility from said second channel by splitting the flow into two or more channels.

System

In another aspect the invention relates to a system for separating a subgroup of cells and/or particles from a mixture of different types of cells and/or particles in a suspension, comprising;

i) a microchip having two inlets (11,12) and at least two outlets (13,14) and at least a first channel.

ii) means to provide pressure, wherein said pressure forces said suspension through an inlet (11) and into at least a pre-alignment channel (15), iii) means to providing a two dimensional acoustic force (15), iv) means to introduce a particle free solution into said channel (12)

v) means for providing a one dimensional acoustic force (16) and vi) means for collecting objects having the same size and/or mass density and/or compressibility from at least two outlets (13,14).

One example of a system is illustrated in the FIGS. 1-5. FIGS. 1 and 2 shows how the suspension comprising the particles which could be a subset of cells are forced into the system (11). The suspension with the particles (FIG. 1, insert c) is then transported through the pre-alignment channel (15) and exposed to a first two-dimensional acoustic force potential acting primarily in the yz-plane (FIG. 1, a-a' and FIG. 2, f-f', respectively) and the cells are focused into two subgroups of cells. The subgroups are then separated into two separate channels and a cell-free solution is introduced into the system through (12). The cell-free solution forces the two subgroups of pre-aligned particles out to positions proximal to the walls of the channel (FIG. 1, inset d). The subgroups of cells are then exposed to a one-dimensional acoustic force (FIG. 1, b-b') (16), which separates cells having different size and/or mass density and/or compressibility from each other into different new subgroups of cells (FIG. 1, inset e). Cells having the same size and/or mass density and/or compressibility are then collected at (13) and (14). The same can be seen in FIG. 5, which is a simplified picture of what happens in the system upon use. Another example is shown in FIG. 7.

Figure 3:
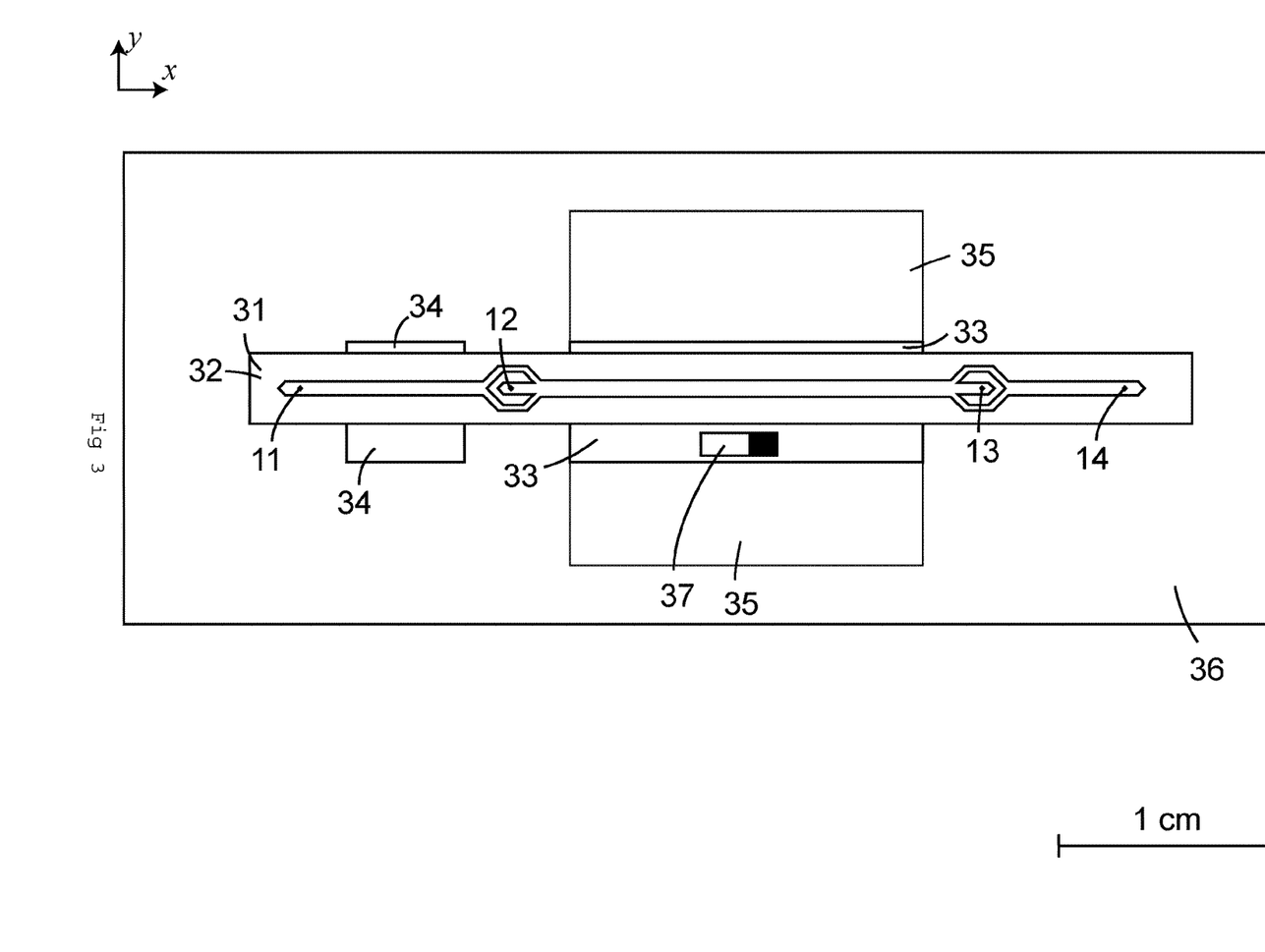
FIG. 3. Drawing suggested realization of the complete device. Top view. To scale.
Figure 4:
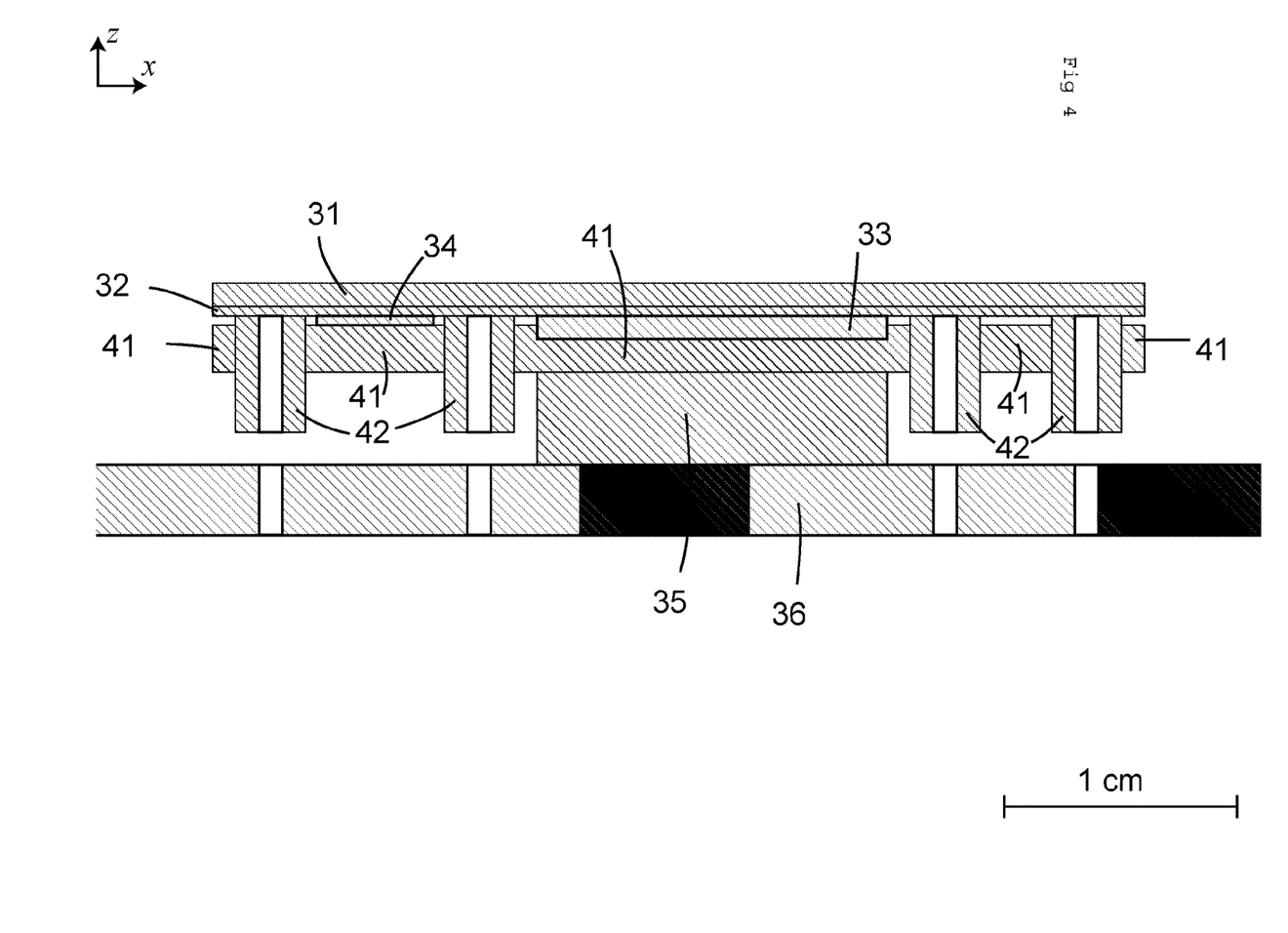
FIG. 4. Drawing suggested realization of the complete device. Side cross sectional view as if cut in half along the vertical center plane. To scale.

In one embodiment the micro chip may be mounted as shown in FIGS. 3 and 4, which are two views of the same micro chip.

In FIG. 3 there is an inlet (11) for the cells and/or particles in a suspension to enter the micro chip. There is an inlet for the particle-free buffer solution (12), which may be any suitable buffer and which depends on what to be separated at the level of separation, i.e., how similar the cells and/or particles are to each other. Examples of buffers may be water, saline solutions, such as 0.9% NaCl or cell media or liquids obtained from a mammal such as blood, serum, urine, milk or other biofluids. Other examples are liquid from the environment such as oil, water from lakes, drinking water or sediments that have been suspended in water. There are at least two outlets, one central (13) and one side outlet (14), where the cells and/or particles are collected.

Over the micro chip with the channel there is a glass cover/ceiling to seal the microchannel (31). There is also silicon substrate (32) wherein the channel segments are etched. There is a transducer (33) for actuation of ultrasound in separation chamber. There is also a second transducer 2 present (34) for actuation of ultrasound for two-dimensional pre-alignment. In this embodiment there is also a Peltier element (35) present to be able to control the temperature in the device. In addition, is an aluminum microscope mounting plate/heat sink (36) present, to absorb excess heat from the Peltier element. A PT-100 thermo resistive temperature sensor (37) is used to monitor temperature for a feed back control loop.

In FIG. 4 an aluminum plate (41) is used for even distribution of heat in the device. There are inlet connectors (42), pieces of silicone tubing, the other references are as shown in FIG. 3 and explained above.

Figure 5:
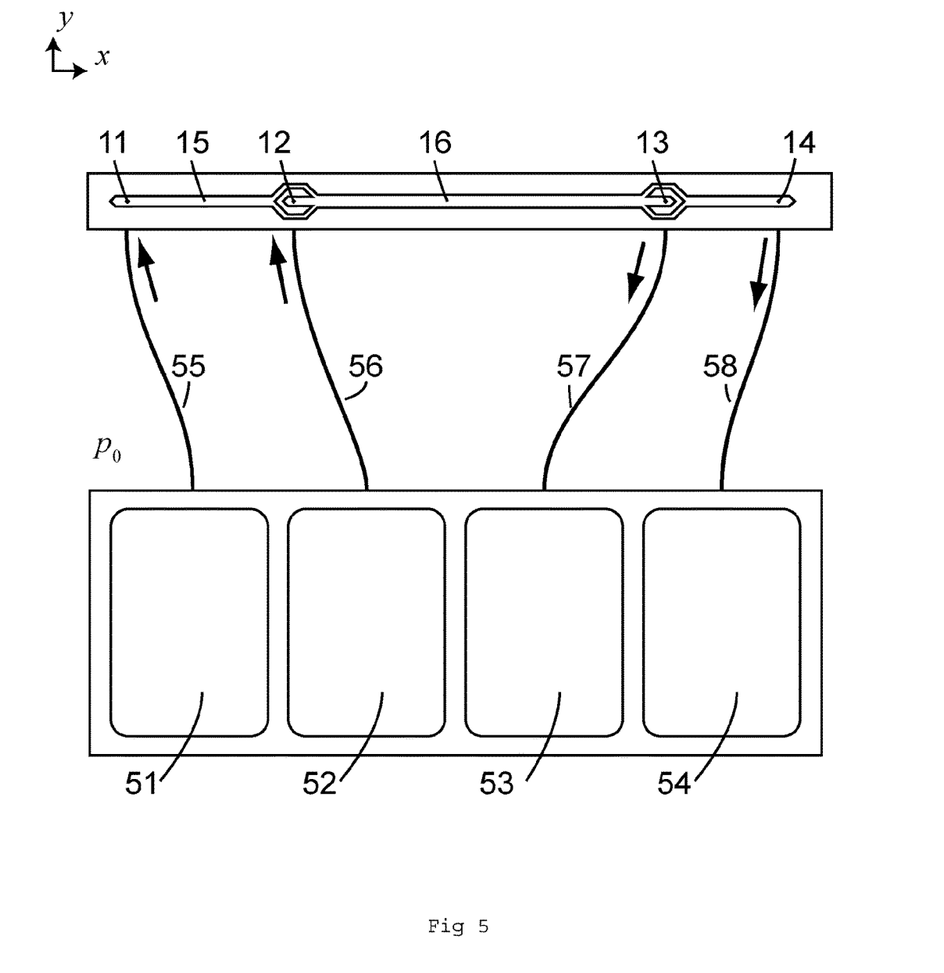
FIG. 5. Schematic of the external fluidics driving the flows in the channel.

In FIG. 5, being a simplified overview of the system in operation. There is a pressure chamber for input cell and/or particle suspension (51), wherein the cells and/or particles are forced into the micro chip. There is one pressure chamber for cell and/or particle free buffer solution (52), which forces the solution into the microchip. There are also two pressure chambers for the central outlet (53) and the sides' outlet (54). There are also four containers present in the chambers, one for the cell and our particle suspension (51), one for the cell and/or particle free buffer solution (52), that may be any solution such as those mentioned above, one container for the central outlet (53) and one for the sides' outlet (54). There are also a number of tubings (55, 56, 57 and 58) that allows the transfer of the liquids from the chambers (51) and (52) and the two chambers (53) and (54).

In one embodiment of the invention the acoustic separation system is operated under iso-thermal conditions since thermal fluctuation may in some embodiments severely influences the acoustic properties of the microchannel acoustic resonators and hence the separation outcome. This may be realized by mounting the microfluidic acoustic separation chip on a Peltier-element that is computer controlled via a temperature sensor feedback at the separation chip vicinity. Thereby the temperature over the whole micro chip is maintained at the same level. If the temperature is too high it might influence the cells and/or the particles. One example being when cells are to be separated that later are to be transferred into a mammal, such as a human being. If the cells are exposed to too high temperatures they get stressed or may die and cannot be transferred back to the subject in need of those cells.

The size of the microchannel constitutes an upper limit of the size of the cells and/or particles to be separated. The cells and/or particles to be separated may vary in shape and size ranging from 1 µm to 50 µm, such as 1-5 µm, 1-25 µm, 5-50 µm, 5-40 µm, 5-30 µm, 5-25 µm, 8-25 µm, or 8, 9, 10, 11, 12, 13, 14, 15, 16, 17, 18, 19 or 20 µm, or from 10-20 µm or 10-15 µm. The cells or particles may have a volume ranging from 0.0005 to $70 \times 10^{-15}$ m$^3$, such as $0.0005\text{-}0.003 \times 10^{-15}$, $0.0005\text{-}0.07 \times 10^{-15}$ m$^3$, $0.0005\text{-}8 \times 10^{-15}$ m$^3$, $0.05\text{-}0.10 \times 10^{-15}$ m$^3$, $0.07\text{-}70 \times 10^{-15}$ m$^3$, $0.07\text{-}35 \times 10^{-15}$ m$^3$, $0.07\text{-}14 \times 10^{-15}$ m$^3$, $0.07\text{-}8 \times 10^{-15}$ m$^3$, $0.25\text{-}6 \times 10^{-15}$ m$^3$ $0.3\text{-}8 \times 10^{-15}$ m$^3$, $0.07\text{-}35 \times 10^{-15}$ m$^3$ or $0.5\text{-}15 \times 10^{-15}$ m$^3$.

Thereby cells, including bacterial cells, as well as most of the cells present in a mammal are included. The cells may be any kind of eukaryotic to prokaryotic cells and examples includes both mammalian cells as well as bacterial cells. Specific examples are cancer cells, platelets, red blood cells, white blood cells (such as: neutrophils, eosinophils, basophils, lymphocytes, monocytes and macrophages), fat cells and *Escherichia coli*.

Said particles may for example be any kind of beads that often are used to separate different biological parts from each other, such as beads onto which antibodies of recognition elements can be coupled to separate biological parts from a suspension of different biological parts. One example being when antibodies are coupled to beads such as polymer beads, magnetic beads and silica beads wherein the antibodies are used to separate antigens from a sample, such as a biological sample.

Figure 8:
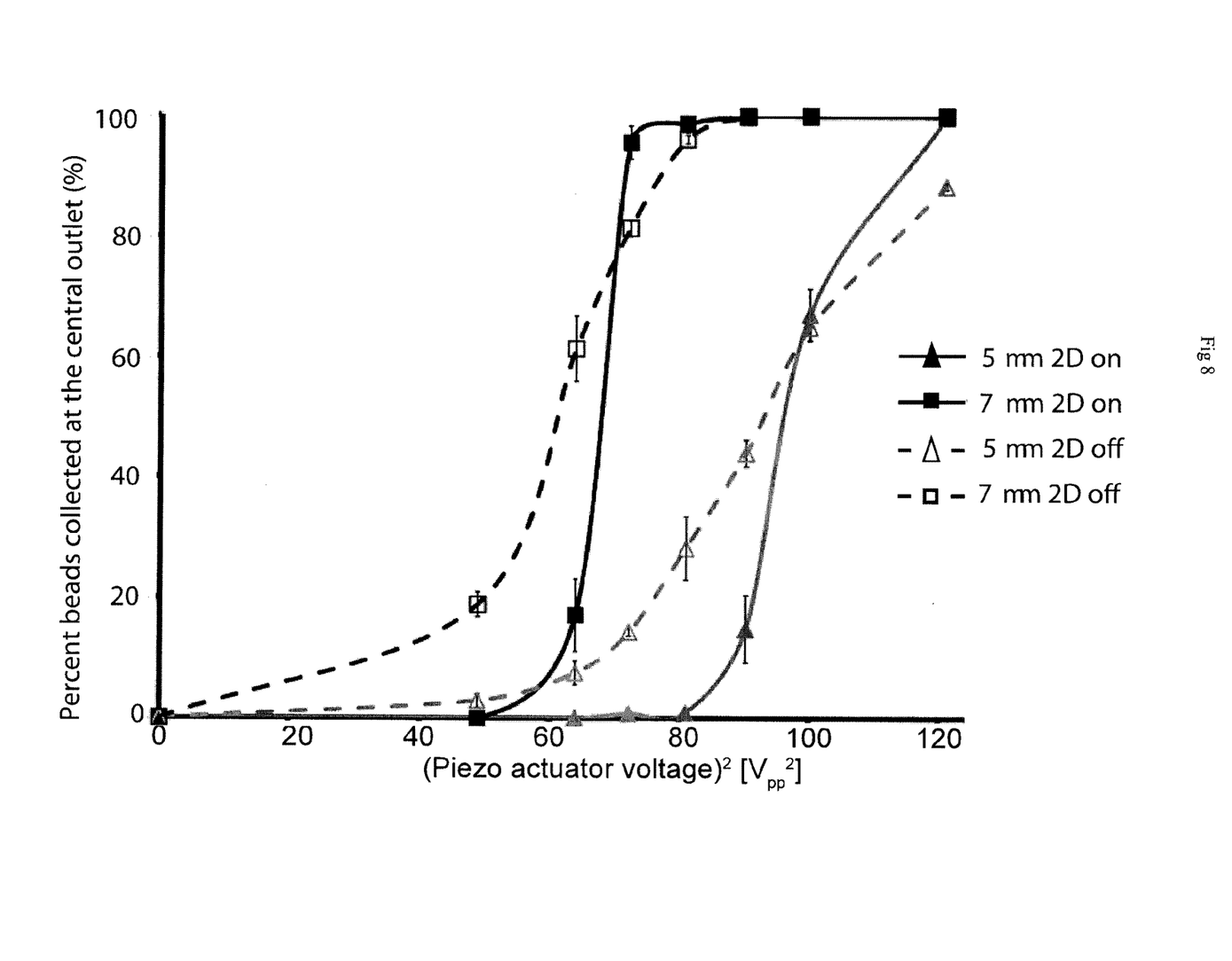
FIG. 8. Graph showing the effect of pre-focusing for a sample mix containing 5 μm and 7 μm polystyrene particles.

In example 3 it is demonstrated the improved separation of 5 and 7 micrometer polystyrene particles as 2 dimensional pre-alignment is employed, as shown in FIG. 8.

The width of said channels may vary between 50 µm to 2000 µm, such as 50-1000, 150-750 µm, 300-750 µm. The width is defined by the size of desired wavelength to be suited in the system and method to focus the different cells and/or particles, One example wherein the invention could be used is in the area of cancer. The system may be useful for discrimination of latent/indolent cancers versus invasive cancers associated with high risk of disease morbidity. It may also be used for the detection of disease recurrence, progression, and response to therapeutic intervention.

Contrary to current clinical practice where CTCs are isolated using immuno-affinity-based techniques (i.e. Veridex—CellSearch®), the invention allows label free separation of CTCs from blood cells. Therefore the invention may potentially also isolate currently undiscovered sub populations of CTCs, i.e. cells that do not express high enough levels of EpCAM for successful conventional immunoaffinity extraction.

Cancer is continually being diagnosed at increasingly earlier stages. Nevertheless, many patients continue to succumb to metastatic disease and for patients with local or distant dissemination the prognosis is still poor. It is believed that tumors spread to new locations by the means of circulating tumor cells (CTCs). CTCs are defined as tumor cells circulating in the peripheral blood, which are shed from the primary tumor or its metastases. CTCs have been found in the blood of epithelial cancer patients with metastatic disease. In addition, CTCs have also been detected in patients with an apparent solid localized tumor, but are extremely rare in healthy persons, indicating that CTCs are shed to the bloodstream even before the onset of metastatic disease.

An association between the presence of CTC in the blood and clinical relevance has been demonstrated in patients with different forms of epithelial cancer. CTCs have been found to be an independent predictor of both progression-free survival and overall survival in patients with metastatic disease. Reported discrepancies may very well be due to differences between various kinds of epithelial cancers, but also to the scarcity of CTCs in the peripheral blood system, generating an immense challenge in detection of tumor cells in clinical samples. There may be as few as one CTC in a billion blood cells.

Extraction and analysis of CTCs from peripheral blood has recently emerged to monitor metastatic cancer stages and to assess therapeutic efficacy of different treatment modalities, either by cell count or by gene expression profiling.

Examples of different kinds of cancer that the method and system could be used for includes solid tumors, such as those mentioned above, prostate, colo-rectal, breast, lung adenocarcinomas, NSCLC, ovarian, pancreatic, GIST, renal cancers, urothelial cancers in bladder or kidney, melanomas, mesotheliomas and gliomas.

Following examples are intended to illustrate but not to limit the invention in any manner, shape, or form, either explicitly or implicitly.

EXAMPLES

Experimental Setting

A microchannel structure and holes for inlets and outlets was KOH etched in a <100> silicon wafer of thickness 350 µm and cut to the dimensions 40 mm by 3 mm (32). A piece of borosilica glass (31) (40 mm by 3 mm by 1 mm) was anodically bonded to seal the channel. Inlets and outlets comprises of pieces of silicone tubing (42) which are glued to the backside of the chip to connect tubing for external fluidics.

All parts of the chip assembly were glued together. From bottom and up sandwiched together: an aluminum mounting plate also serving as heat sink, a Peltier element (35) (15 mm by 15 mm), an aluminum bar (41) (40 mm by 3 mm by 2 mm) with holes drilled to match the radius of the silicone inlet/outlet tubing, two piezoceramic actuators, one ~5 MHz transducer (34) (5 mm by 5 mm) positioned below the pre-alignment channel, and one ~2 MHz transducer (33) (15 mm by 5 mm) placed under the separation channel, and the acoustophoresis chip, see FIGS. 3 and 4. A Pt100 thermo-resistive element for temperature measurement, was glued onto the 2 MHz piezoceramic actuator alongside the acoustophoresis chip, see FIG. 3.

The piezoceramic transducers are driven by two signal-generators equipped with signal power amplifiers. The acoustic resonances can be controlled by tuning the frequency and voltage over the transducers.

Cells/microparticles in suspension enter a first pre-focusing channel (15) at a flow rate of 50 or 70 µL min$^{-1}$. A 5 MHz resonance in the yz-plane focus particles in two narrow bands, see FIGS. 1 and 2. Clean buffer medium enters through (12) at a volume flow rate of 450 or 490 µL/min and divides the pre-aligned particles further so that the stream of particles are pushed close to the walls of a separation channel (16). A 1.94 MHz resonance along the y-coordinate only focuses the particles towards the channels vertical center plane. At the end of the separation channel the flow is split up in a trifurcation outlet (13 and 14). The central outlet (13) volume flow is set to 150 or 280 µL/min and the volume flow rate in the combined side's outlet (14) was 250 or 280 µL/min.

Example 1

Separation of 5 µm and 7 µm Polystyrene Beads

Sample preparation. A mixture of 5 µm and 7 µm polystyrene beads (~5 mg mL$^{-1}$) was added to a solution of Triton X100 (0.01%) in PBS.

Flow system setup. The volume flow in the system is controlled by three 10 mL glass syringes (1010 TLL, Hamilton Bonaduz AG, Bonaduz, Switzerland), two of which are mounted on the same syringe pump (WPI sp260p, World Precision Instruments Inc., Sarasota, Fla., USA) maintaining a volume flow $Q_3=Q_4=250$ µL min$^{-1}$ in both the central and the combined side's outlet, respectively (see FIG. 6 for definition of $Q_i$). The flow rates of these two syringes dictate the total volume flow ($Q_{total}=500$ µL min$^{-1}$) rate in the main channel. The third syringe, mounted in a separate syringe pump (neMESYS, Cetoni GmbH, Germany), infuses cell-free buffer solution in the central inlet to the channel at a volume flow rate corresponding to 90% of the total flow rate ($Q_2=450$ µL min$^{-1}$). Particle mixture was drawn into the side's inlet from the bottom of a test tube, at atmospheric pressure, at a flow rate of 10% of the total volume flow rate ($Q_1=50$ µL min$^{-1}$) dictated by the net flux created by the three syringes. Two 6-port, 2-way sample-loops (V-451, Upchurch Scientific, Oak Harbor, Wash., USA) each of volume 100 µL, were connected in series with the outlets to probe the separation performance while running the system.

The inlet tubing of the device was immersed into a test tube containing ~1 mL of particle mixture. To minimize any effect of sedimentation of particles in the test tube, the sample was mixed gently by pipetting up and down during sample processing. Flow was allowed to stabilize in the system for a few seconds before switching the two sample loops to collection mode. The loops were sampled 3 times in the course of each experiment to enable analysis of the particle content of the side and center outlet, respectively.

Analysis of acquired outlet fractions. After acoustophoresis the microbeads in the central respectively side outlet fractions were enumerated by flow cytometry (FACS Canto II flow cytometer and the FACSDiva software, BD Biosciences). The two bead sizes are clearly distinguishable in a forward/side scatter plot.

Acoustophoresis particle separation procedure. The ultrasound actuation frequency was adjusted to approximately 4.79 MHz in the first two-dimensional pre-focusing channel and in the second, separation channel, a fundamental resonance at approximately 1.94 MHz was used. In a first experiment the voltage amplitude over the 2 MHz separation channel transducer (33) was varied from 0 to 11 Vpp, while the 5 MHz pre-alignment transducer (34) was turned off. After turning on the pre-alignment transducer the voltage to the separation transducer was again varied from 0 to 11 Vpp. Results are shown in FIG. 8. It is clear that the two-dimensional pre-alignment of microbeads improve the ability to discriminate between the two bead sizes.

Example 2

Extraction of Tumor Cells from Blood

Cell culture and healthy blood donors. The human prostate cancer cell line DU145, was obtained from the American Type Tissue Collection (ATTC) and grown according to ATTC recommendations. Blood was acquired from healthy volunteers at the Blood bank at Lund University Hospital, (Lund, Sweden).

Cell immunostaining, preparation and spiking experiments. For processing of 1 mL sample, an aliquot of 100 µL blood was incubated with the fluorochrome-conjugated antibody CD45-APC (diluted 1:5) or control IgG-APC (both from BD Bioscience, San Jose, Calif.), in room temperature for 20 min, followed by isotonic RBC lysis for 15 minutes. The supernatant containing lysed erythrocytes was discarded after 5 minutes centrifugation at 500 g, with subsequent washing steps with FACS buffer (PBS, 1% BSA, 2 mM EDTA). Depending on application, the cells were either fixed in 2% paraformaldehyde (PFA) or not before the cell pellet was resuspended in FACS buffer. Prostate cancer cells were detached by trypsin/EDTA followed by repeated washing with FACS buffer. Cells were resuspended in FACS buffer containing fluorochrome-conjugated antibody EpCAM-PE (diluted 1:5) or control IgG-PE antibody (both from BD Bioscience), and incubated on ice for 40 min. The cancer cells were either fixed by 2% PFA or not before they were resuspended in FACS buffer. Erythrocyte lysed blood (diluted 1:10), in PBS was spiked with $2.5\times10^5$ mL$^{-1}$ DU145 cells.

Flow system setup. The volume flow in the system is controlled by three 10 mL glass syringes (1010 TLL, Hamilton Bonaduz AG, Bonaduz, Switzerland), two of which are mounted on the same syringe pump (WPI sp260p, World Precision Instruments Inc., Sarasota, Fla., USA) maintaining a volume flow $Q_3=Q_4=280$ µL min$^{-1}$ in both the central and the combined side's outlet, respectively (see FIG. 6 for definition of $Q_i$). The flow rates of these two syringes dictate the total volume flow ($Q_{total}=560$ µL min$^{-1}$) rate in the main channel. The third syringe, mounted in a separate syringe pump (neMESYS, Cetoni GmbH, Germany), infuses cell free buffer solution in the central inlet to the channel at a volume flow rate corresponding to ⅞ of the total flow rate ($Q_2=490$ µL min$^{-1}$). Particle mixture was drawn into the side's inlet from the bottom of a test tube, at atmospheric pressure, at a flow rate of ⅛ of the total volume flow rate ($Q_1=70$ µL min$^{-1}$) dictated by the net flux created by the three syringes. Two 6-port, 2-way sample loops (V-451, Upchurch Scientific, Oak Harbor, Wash., USA) each of volume 100 µL, were connected in series with the outlets to probe the separation performance while running the system.

The inlet tubing of the device was immersed into a test tube containing ~1 mL of particle mixture. To minimize any effect of sedimentation of particles in the test tube, the sample was mixed gently by pipetting up and down during sample processing. Flow was allowed to stabilize in the system for a few seconds before switching the two sample loops to collection mode. The loops were sampled 3 times in the course of each experiment to enable analysis of the particle content of the side and center outlet, respectively.

Acoustophoresis cell separation procedure. The ultrasound actuation frequency was adjusted to approximately 5.0 MHz in the first two dimensional pre-focusing channel and in the second, separation channel, a fundamental resonance at approximately 2 MHz was used.

Analysis of acquired outlet fractions. After acoustophoresis the fluorescently labeled cells in the central respectively side outlet fractions were enumerated by flow cytometry. WBCs were characterized as CD45 positive and EpCAM negative, whereas the tumor cells were denoted EpCAM positive and CD45 negative. The fluorescence was quantified by a FACS Canto II flow cytometer and the FACSDiva software (BD Biosciences).

Figure 9:
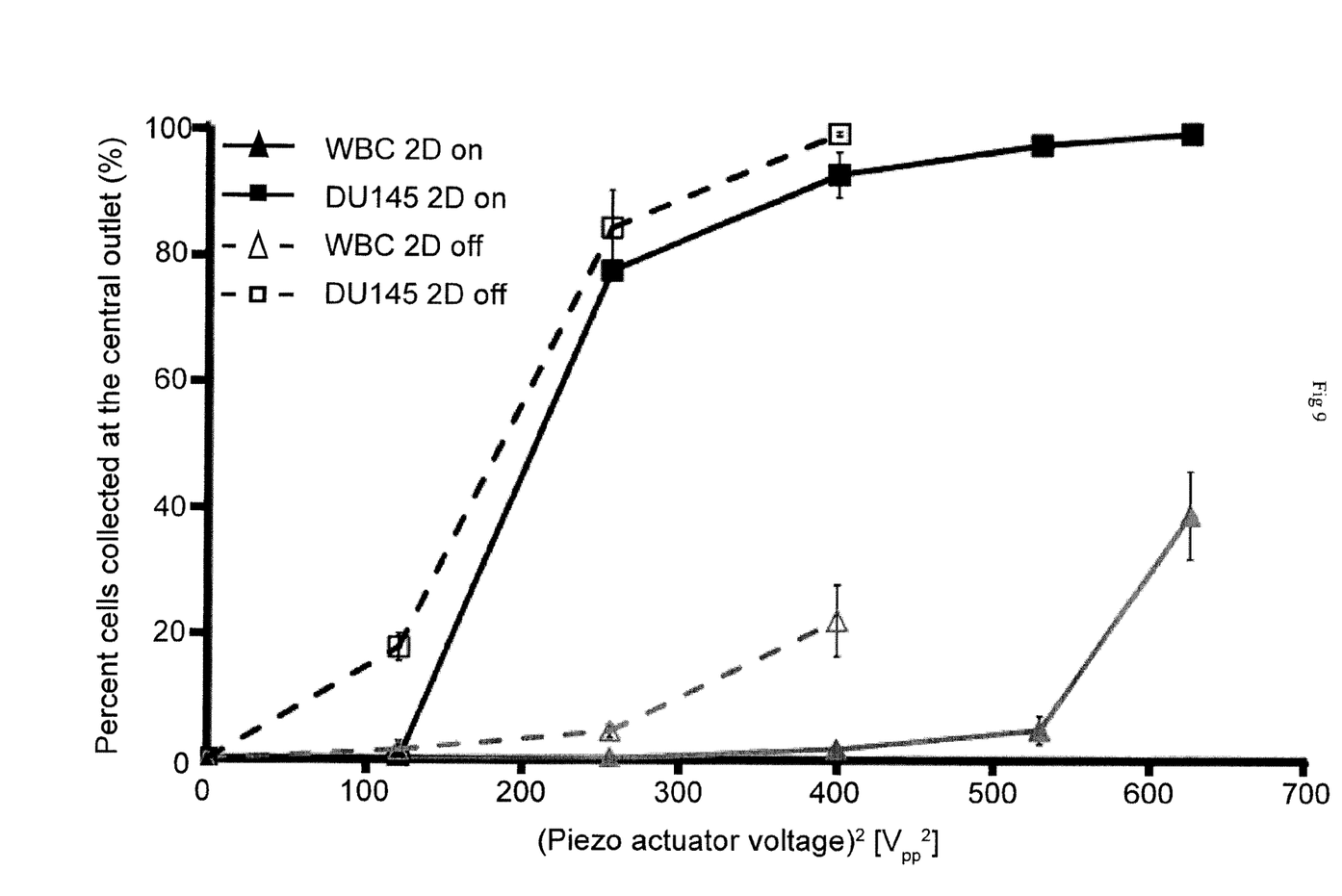
FIG. 9. Graph showing the effect of pre-focusing for a sample mix containing DU145 cancer cells and white blood cells.

Acoustic pre-alignment vs. no pre-alignment. The effect of pre-alignment of cells was tested on a cell mixture of DU145 and WBCs. The cells were processed through the microchip in the presence or absence of ultrasound in the pre-alignment channel and actuated with increasing voltage amplitudes in the separation channel. Flow cytometry was used to evaluate the cell composition of the center and side outlet fractions. Pre-alignment of cells into the pressure nodes of the standing wave allowed them to enter the separation channel at the same height and speed generating an improved and more stable separation of cancer cells from WBC, see FIG. 9.

Analyses of experimental outcome. To analyze the experimental outcome, the numbers of cancer cells and WBCs in the central and side's outlets was determined by flow cytometry. Three measures were calculated to profile the separation performance: Tumor cell capture efficiency—the number of cancer cells in the central outlet relative to all detected cancer cells in both outlets. WBC depletion efficiency—the number of WBCs in the side outlet relative to all detected WBCs in both outlets. Tumor cell capture purity—the number of cancer cells in the central outlet relative to all detected cells in the central outlet.

Varying retention time. The ability to discriminate tumor cells from WBCs was shown to be highly dependent on cell retention time in the chip. Retention time was assessed by varying the total flow rate in the chip while maintaining the relative flow ratios in inlets and outlets, at constant piezoactuator driving voltage and frequency.

Figure 10:
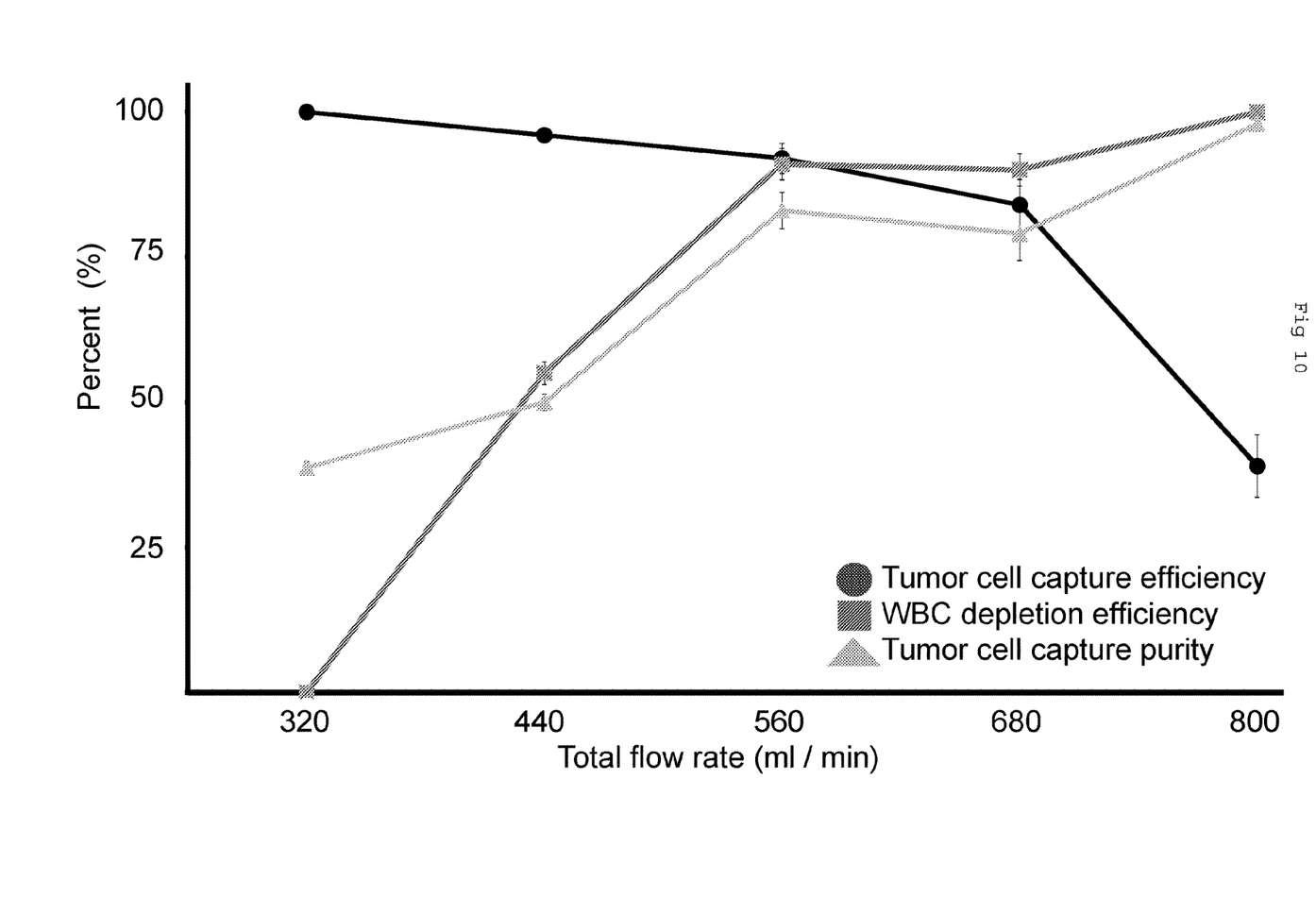
FIG. 10. Graph showing the effect of changing the flow rate for a sample mix containing DU145 cancer cells and white blood cells.

Depending on desired application, complete WBC depletion or full DU145 cell recovery, (but to the cost of a decrease in WBC depletion), can be achieved, FIG. 10. Sample process rate was kept at ⅛ of the total flow rate and, thus, ranged from 40 µL min$^{-1}$ to 100 µL, min$^{-1}$.

Above sample processing rates do not constitute an upper limit of the capacity of the system. By increasing the amplitude of the piezo actuator drive voltage, the sample throughput can be raised to levels well above 10 mL h$^{-1}$ while maintaining similar separation behavior as shown for lower flow rates (data not shown).

Effect of outlet flow ratio. In FIG. 10 the sample inlet flow and the central buffer inlet flow had a ratio of 1:7. This arrangement leads to a dilution of cells in the two outlets were the flow has been kept constant at a ratio of 1:1 to ensure equal retention time in the two sample collection loops. By adjusting the side-to-center outlet flow ratio to 7:1, direct comparisons can be made between cells detected in central outlet fraction, and input sample composition.

This strategy of tuning the hydrodynamic aperture in the central outlet offers means to optimize the separation conditions. By tuning the outlet ratio, optimal enrichment can be achieved. The change in outlet flow configuration results in high tumor cell capture efficiency while maintaining a low degree of WBC, and at least 800 times enrichment of tumor cells from WBC have been achieved. A decreased outlet ratio between central and side outlets flow (finer hydrodynamic aperture) mediates a longer distance for cells to migrate to reach the central outlet and thereby increases the WBC exclusion efficiency.

Example 2 describes the first experimental evidence that acoustophoresis is a viable route towards efficient isolation of CTCs either as a stand-alone technique or hyphenated to other serially linked CTC separation techniques.

A key feature of the proposed CTC isolation method is that unlabelled fixed or live cells may be addressed. In the latter case live cell recovery can pave the way towards post separation culturing and expansion of extracted CTCs for in depth analysis of genetic profile and diversity and hence improve diagnostic and prognostic preconditions.

The invention claimed is:

1. A micro scaled method for separating a subgroup of cells and/or particles from a mixture of different types of cells and/or particles in a suspension, comprising the steps of:
   i) subjecting a suspension to pressure, wherein said pressure forces said suspension into one inlet and into at least one pre-alignment channel present on a microfluid chip;
   ii) subjecting said suspension to a two dimensional acoustic force directed perpendicular to the length direction of the pre-alignment channel, thereby forcing said mixture of cells and/or particles away from the walls, floor, and ceiling of the pre-alignment channel and confining said mixture of cells and/or particles into one or more discrete positions in the plane transverse to the length direction of the pre-alignment channel;
   iii) forcing said mixture of cells and/or particles and infusing cell free buffer solution through a second inlet simultaneously into at least one separation channel, wherein said mixture of cells and/or particles are forced towards the walls of the separation channel;
   iv) subjecting said cells and/or particles to a one dimensional acoustic force directed perpendicular to the length direction of the separation channel; and
   v) collecting cells and/or particles having the same size and/or mass density and/or compressibility from said separation channel present on the microfluid chip through at least two outlets, wherein the two dimensional acoustic force is actuated by a single transducer.

2. The method according to claim 1, wherein the two dimensional acoustic force in step ii) consists of ½ wavelength and 1 wavelength perpendicular to each other.

3. The method according to claim 1, wherein said one dimensional acoustic force in step iv) consists of ½ wavelength.

4. The method according to claim 1, wherein said two dimensional acoustic force is caused by a frequency of from 1 to 10 MHz.

5. The method according to claim 1, wherein said method is maintained at a constant temperature.

6. The method according to claim 1, wherein the height or the width of the pre-alignment channel is from 75 um to 800 um.

7. The method according to claim 1, wherein said cells and/or particles have a size of from 1-50 µm.

8. The method according to claim 1, wherein said cells are cancer cells and said suspension is blood.

9. The method according to claim 1, wherein the two dimensional acoustic force is caused by separate frequencies of vibration for height and width of the pre-alignment channel.

10. The method according to claim 1, wherein the two dimensional acoustic force is caused by a frequency of vibrations f, and wherein the width w and the height h of the pre-alignment channel are related to the frequency f by $$f = \frac{cn}{2w} = \frac{cm}{2h}$$

wherein m and n are integers and c is the speed of sound in the suspension.

11. The method according to claim 1, wherein the single transducer comprises a piezoceramic actuator, and wherein the piezoceramic actuator is attached to the microfluid chip below the pre-alignment channel.

12. A micro system for separating a subgroup of cells and/or particles from a mixture of different types of cells and/or particles in a suspension, comprising:
   i) a micro chip having at least one pre-alignment channel and at least one separation channel, with at least two inlets and at least two outlets;
   ii) means for providing pressure, wherein said pressure, forces said suspension into the first inlet;
   iii) means for providing a two dimensional acoustic force, wherein said two dimensional acoustic force is directed perpendicular to said pre-alignment channel thereby forcing said mixture of cells and/or particles away from the walls, floor, and ceiling of the pre-alignment channel and confining said mixture of cells and/or particles into one or more discrete positions in the plane transverse to the length direction of the pre-alignment channel;
   iv) means for infusing cell free buffer in said second inlet;
   v) means for providing a one dimensional acoustic force, wherein said one dimensional acoustic force is directed perpendicular to said separation channel; and
   vi) means for collecting cells and particles, having the same size and/or mass density and/or compressibility, from said separation channel, wherein the means for providing the two dimensional acoustic force comprises a single transducer.

13. The micro system according to claim 12, wherein the two dimensional acoustic force is caused by separate frequencies of vibration for height and width of the pre-alignment channel.

14. The micro system according to claim 12, wherein the two dimensional acoustic force is caused by a frequency of vibration f, and wherein the width w and the height h of the pre-alignment channel are related to the frequency f by $$f = \frac{cn}{2w} = \frac{cm}{2h}$$

wherein m and n are integers and c is the speed of sound in the suspension.

15. The micro system according to claim 12, wherein the single transducer comprises a piezoceramic actuator, and wherein the piezoceramic actuator is attached to the microchip below the pre-alignment channel.

* * * * *